(12) United States Patent
Woodard et al.

(10) Patent No.: US 12,329,395 B2
(45) Date of Patent: Jun. 17, 2025

(54) METHODS AND APPARATUS FOR MINIMALLY INVASIVE BUNION SURGERY

(71) Applicant: WRIGHT MEDICAL TECHNOLOGY, INC., Memphis, TN (US)

(72) Inventors: Joseph Ryan Woodard, Memphis, TN (US); Johnny McGEE, Halls, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 312 days.

(21) Appl. No.: 17/933,640

(22) Filed: Sep. 20, 2022

(65) Prior Publication Data
US 2023/0149031 A1     May 18, 2023

Related U.S. Application Data (60) Provisional application No. 63/264,246, filed on Nov. 18, 2021.

(51) Int. Cl.
*A61B 17/17* (2006.01)
*A61B 17/88* (2006.01)

(52) U.S. Cl.
CPC ...... *A61B 17/1775* (2016.11); *A61B 17/8897* (2013.01)

(58) Field of Classification Search
CPC .............. A61B 17/1775; A61B 17/152; A61B 17/8897; A61B 2017/565; A61F 2/4606
See application file for complete search history.

(56) References Cited

U.S. PATENT DOCUMENTS

| | | | | |
|---|---|---|---|---|
| 6,030,391 | A * | 2/2000 | Brainard | A61B 17/15 606/82 |
| 2007/0265634 | A1 * | 11/2007 | Weinstein | A61B 17/15 606/87 |
| 2013/0190765 | A1 | 7/2013 | Harris et al. | |
| 2017/0014173 | A1 * | 1/2017 | Smith | A61B 17/1775 |
| 2018/0250024 | A1 | 9/2018 | Woodard et al. | |

(Continued)

FOREIGN PATENT DOCUMENTS

| CN | 209499835 U | 10/2019 |
|---|---|---|
| WO | 2020180598 A1 | 9/2020 |

OTHER PUBLICATIONS

Partial European Search Report issued in connection with European Patent Application No. 22198088.1.

(Continued)

*Primary Examiner* — David W Bates
(74) *Attorney, Agent, or Firm* — DUANE MORRIS LLP (57) ABSTRACT

A system and method for performing a percutaneous bunionectomy. The system including a jig, which subsequent to attachment and performance of an osteotomy on the bone, uses a rack and pinion mechanism to translate the separated portion of the bone to a surgeon determined displacement λ. A locking mechanism maintains the desired displacement of the bone portions and allows the surgeon, with use of an attached visual guide, to insert a k-wire through the bone portions to serve as a guide wire for the internal fixation that maintains the displacement during the healing. The system removes the requirement that the surgeon manually maintain the desired displacement while inserting the guide wire.

23 Claims, 9 Drawing Sheets

(56) References Cited

U.S. PATENT DOCUMENTS

| | | | |
|---|---|---|---|
| 2020/0060698 A1 | 2/2020 | Woodard et al. | |
| 2020/0093501 A1* | 3/2020 | Patel | A61B 17/1728 |
| 2021/0244443 A1 | 8/2021 | Coyne et al. | |
| 2021/0330335 A1* | 10/2021 | Boffeli | A61B 17/151 |
| 2021/0369287 A1* | 12/2021 | Boffeli | A61B 17/8061 |
| 2022/0054171 A1* | 2/2022 | Carlo, III | A61B 17/1775 |
| 2022/0401139 A1* | 12/2022 | Korman | A61B 17/8897 |
| 2023/0053657 A1* | 2/2023 | Korman | A61B 17/66 |
| 2023/0056081 A1* | 2/2023 | Korman | A61B 17/1775 |
| 2023/0149031 A1* | 5/2023 | Woodard | A61B 17/1775 606/87 |
| 2023/0190352 A1* | 6/2023 | Coyne | A61B 17/8095 606/87 |
| 2023/0240720 A1* | 8/2023 | Schmidt | A61B 17/151 623/53 |

OTHER PUBLICATIONS

Extended Search Report issued in connection with corresponding European Patent Application No. 22198088, filed Jul. 3, 2023, 17 pages.

* cited by examiner

METHODS AND APPARATUS FOR MINIMALLY INVASIVE BUNION SURGERY

CROSS-REFERENCE TO THE RELATED APPLICATION

This application claims priority under 35 U.S.C. § 119(e) to U.S. Provisional Application No. 63/264,246, filed on Nov. 18, 2021, the entire contents of which are incorporated herein by reference

TECHNICAL FIELD

The disclosed subject matter relates generally a guide system and method to aid an orthopedic surgeon in translating the distal bone fragment and inserting a k-wire into the bone.

BACKGROUND

Minimally invasive bunion surgery, also known as percutaneous bunionectomy, is a surgical procedure that seeks to correct a bunion deformity by utilizing a small incision. Hallux Valgus is a deformity of the big toe joint wherein a deviation of the big toe towards the lesser toes results in a prominent bump, or bunion.

During a minimally invasive bunion procedure, a surgeon will create an osteotomy in the first metatarsal and then translate a portion of the metatarsal longitudinally prior to installing fixation e.g., Kirschner wire ("k-wires"). Prior art methods require one instrument to be used for translation of the distal bone fragment and another to be used for k-wire targeting. Maintaining adequate translation while applying and using the targeting guide can be cumbersome and represents a challenge to the surgeon.

During any surgery, and minimally invasive surgery in particular, surgeons utilize K-wires to both stabilize the position of bones and to serve as guide wires for screw insertion. It is not uncommon for surgeons to require multiple k-wire insertions before they place the guide wire into the desired position. However, repeated k-wire insertions require time, increase frustration during the procedure, and represent micro-injuries to the bone that the body must heal in addition to the surgical correction.

Current guides/jigs for use in MIS bunion surgery require the surgeon to continuously hold the translation instrument in place in order to maintain the desired translation while targeting the fixation wires. One example, US Patent Application Publication 2020/0060698 entitled SCREW TARGETING GUIDE SYSTEM AND METHOD describes a handheld targeting guide for MIS bunion surgery, the entirety of which is herein incorporated by reference. The current subject matter presents a jig that combines both features into one instrument and independently maintains the desired translation while the surgeon places the fixation wires.

Reducing the number of instruments, maintaining the desired translation, and enabling the surgeon's hands to focus on k-wire insertion would be beneficial to both the surgeon and patient. Thus, given the deficiencies in the prior art, there remains a need for an improved apparatus to aid in MIS bunion surgery.

SUMMARY

The embodiments described herein are directed to a system, apparatus, and method for bunion correction utilizing a guide for translating the metatarsal head with respect to the metatarsal shaft subsequent an osteotomy and guiding a k-wire utilized in the fixation of the head and shaft in the relative translated position. In addition to or instead of the advantages presented herein, persons of ordinary skill in the art would recognize and appreciate other advantages as well.

In some embodiments, a system for performing a percutaneous bunionectomy is provided. The system including a jig having a body, a shaft contact pad connected to the jig body and conformed to the soft tissue proximate the metatarsal shaft, an arm extending in a longitudinal direction from the jig body, a metatarsal head contact pad connected to the arm and configured to conform to the soft tissue proximate the metatarsal head; a track rigidly connected to the second arm end and movably connected to the jig body and a circular track cooperating with an engagement mechanism of the track, such that a rotation of the track drive results in a lateral movement of the track. The system further includes an alignment guide arm connected to and extending longitudinally from the jig body and a plurality of positioning k-wires, attaching each of the metatarsal head contact pad and the metatarsal shaft contact pad through a multidimensional fixation hole to the metatarsal bone. A guide wire is also provided in the system for insertion through the displaced shaft and head of the metatarsal to assist in the subsequent insertion of a fixation screw.

In some embodiments, a method is provided, the method including the steps of creating an incision in the soft tissue of the foot, positioning a jig upon the soft tissue surrounding the metatarsal bone; securing the jig to the metatarsal bone and, via the incision cutting the metatarsal bone, creating a first portion of the metatarsal and a second portion of the metatarsal. The method further includes translating the jig track to laterally displace the second portion with respect to the first portion; adjusting the visual alignment guide to a desired trajectory; and inserting a fixation k-wire as a screw guide through the first and second portions of the metatarsal such that a fixation screw may permanently fix the bone portions in the laterally displaced position. In the method, the jig is subsequently removed from the metatarsal and the incision is closed.

In yet another embodiment, a translation and insertion jig for insertion of a k-wire is presented. The jig having a body, a shaft contact pad connected to the jig body and conformed to the soft tissue proximate metatarsal shaft, an arm extending in a longitudinal direction from the jig body, a metatarsal head contact pad connected to the arm and configured to conform to the soft tissue proximate the metatarsal head; a track rigidly connected to the second arm end and movably connected to the jig body and a track drive cooperating with an engagement mechanism of the track, such that a rotation of the track drive results in a lateral movement of the track. The system further includes a lock configured to selectively restrain the track from translation relative to the jig body and an alignment guide arm connected to and extending longitudinally from the jig body

BRIEF DESCRIPTION OF THE DRAWINGS

The features and advantages of the present disclosures will be more fully disclosed in, or rendered obvious by, the following detailed descriptions of example embodiments. The detailed descriptions of the example embodiments are to be considered together with the accompanying drawings wherein like numbers refer to like parts and further wherein.

DETAILED DESCRIPTION

The description of the preferred embodiments is intended to be read in connection with the accompanying drawings, which are to be considered part of the entire written description of these disclosures. While the present disclosure is susceptible to various modifications and alternative forms, specific embodiments are shown by way of example in the drawings and will be described in detail herein. The objectives and advantages of the claimed subject matter will become more apparent from the following detailed description of these exemplary embodiments in connection with the accompanying drawings.

It should be understood, however, that the present disclosure is not intended to be limited to the particular forms disclosed. Rather, the present disclosure covers all modifications, equivalents, and alternatives that fall within the spirit and scope of these exemplary embodiments. The terms "couple," "coupled," "operatively coupled," "operatively connected," and the like should be broadly understood to refer to connecting devices or components together either mechanically, or otherwise, such that the connection allows the pertinent devices or components to operate with each other as intended by virtue of that relationship.

Figure 1:
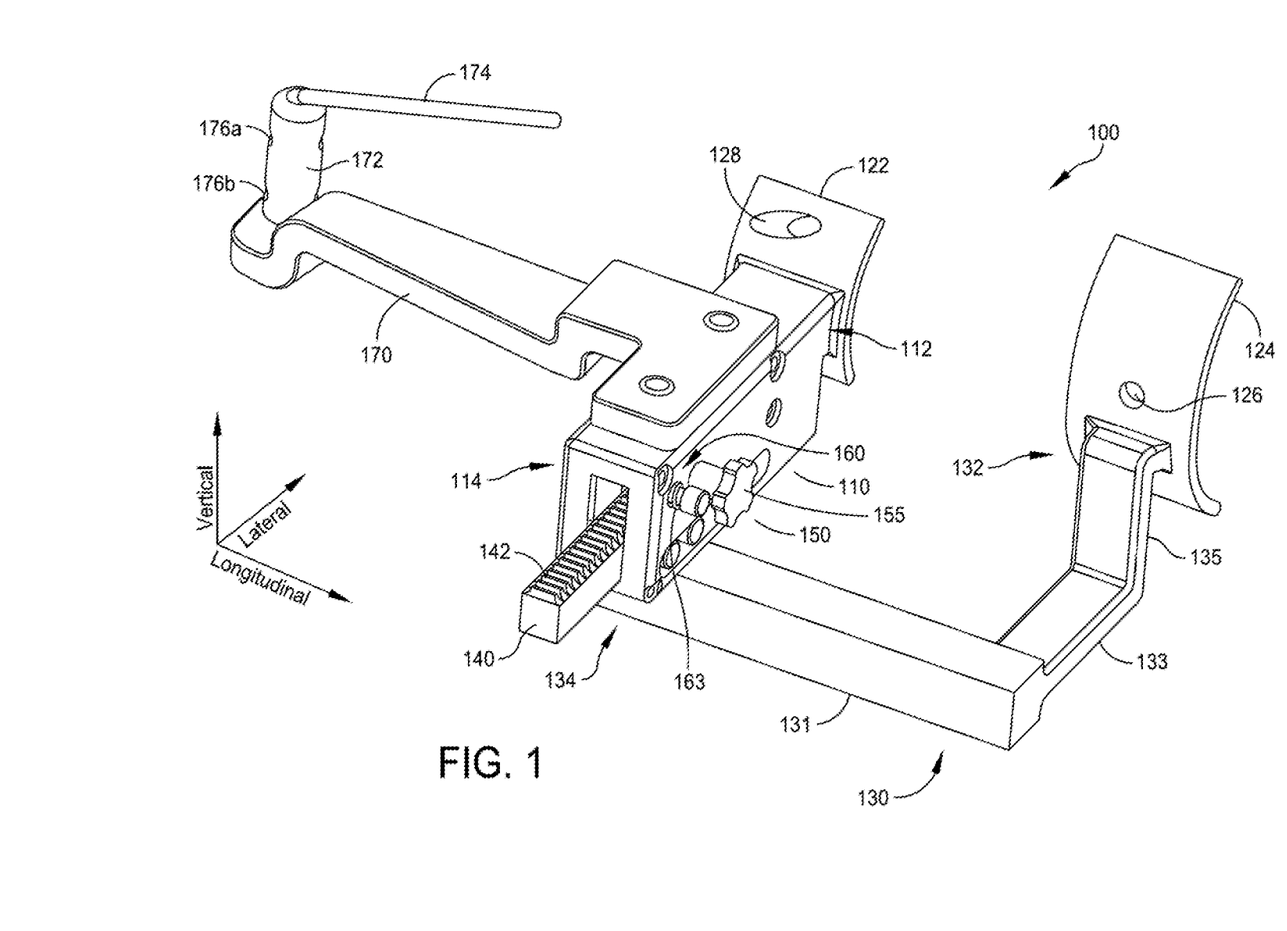
FIG. 1 is an isometric illustration of a translation and insertion jig in accordance with some embodiments of the disclosed subject matter.
Figure 3:
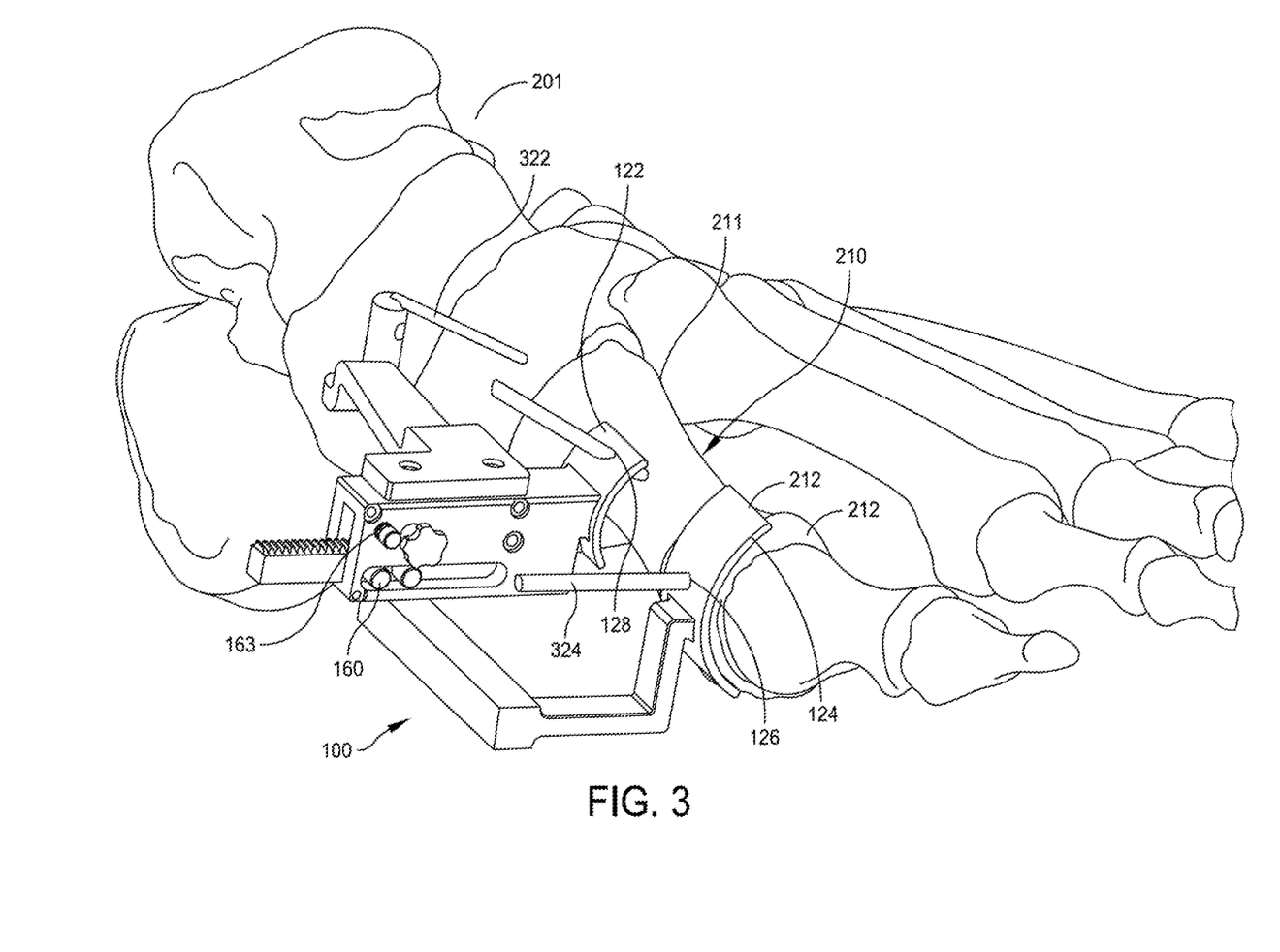
FIG. 3 illustrates the translation and insertion jig secured to the metatarsal bone via k-wires in accordance with some embodiments of the disclosed subject matter.

FIG. 1 illustrates a translation and insertion jig 100 for minimally invasive bunion surgery. The jig includes a body 110 which extends from its first end 112 configured to face the bone to a second end 114. The jig 100 includes a metatarsal shaft contact pad 122 connected to the first end 112 of the jig body 110. The shaft contact pad 122 is preferably conformed to the portion of soft tissue (e.g., skin, muscle, fat, fibrous tissue, blood vessels, or other supporting tissue of the body) covering the foot proximate to the metatarsal shaft to which it is intended to engage (e.g. concave). The contour of the shaft contact pad 122 may be conformed during surgery to match the soft tissue surrounding the bone, or pre-contoured. The shaft contact pad 122 may also be selectable by the surgeon from a plurality of different sizes and shapes, such that the jig 100 may have a set of interchangeable contact pads, or pads that attach to the first end 112. The shaft contact pad 122 along with the head contact pad 124 discussed later, include at least one k-wire insertion hole 126, 128 that allows multi-dimensional fixation (i.e., restraint of relative movement in the vertical, lateral and longitudinal directions) of the pads 122, 124 to the respective shaft and head of the metatarsal bone (as shown in FIG. 3).

Figure 4:
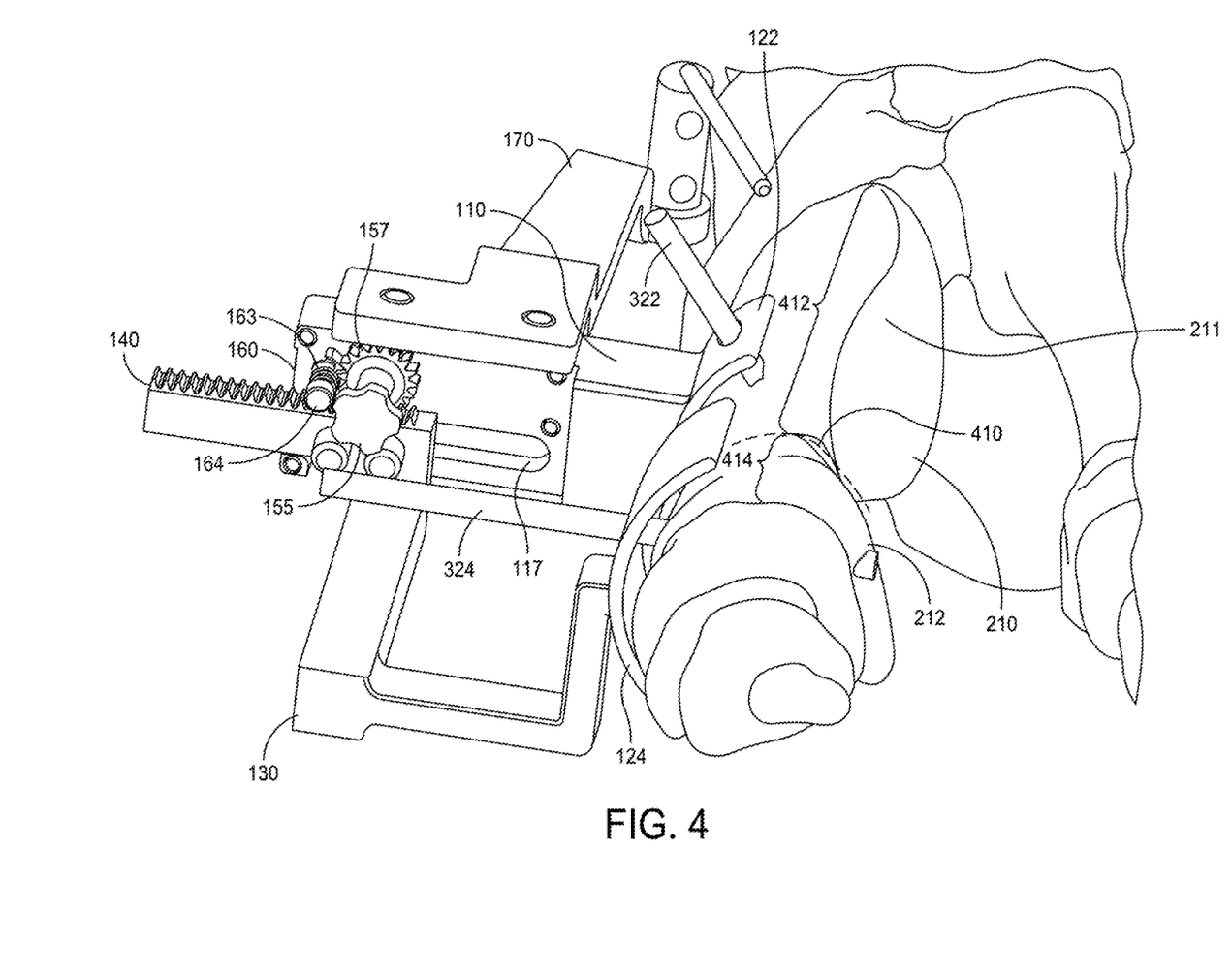
FIG. 4 illustrates the translation and insertion jig attached to the metatarsal bone subsequent an osteotomy of the metatarsal bone and prior to the lateral displacement of the metatarsal bone head via the jig in accordance with some embodiments of the disclosed subject matter.

Within or upon the jig body 110 is a linear track 140 extending in the lateral direction, the track 140 rigidly connected to the second end 134 of the extending arm 130 and movably connected to the jig body 110. The linear track 140 includes an engagement mechanism, which, shown in FIGS. 1-7, is the rack of a rack and pinion mechanism which includes a toothed surface 142. The track 140 alternatively may have a threaded surface such as in a lead screw mechanism. The track 140 is retained to the jig body to allow only lateral movement. FIG. 4 illustrates a groove 117 in the jig body 110 that retains the track 140 in one embodiment, of course other known retention methods are also envisioned. The track 140 may be incremented to enable the surgeon to ascertain the amount of lateral translation and may be further indexed to move one increment (click) at a time, via indentations and ball stops (not shown), or other indexing mechanism known in the art.

The jig 100 has a longitudinal extending arm 130, a second end 134 of the arm 130 attached to a track 140. As with the shaft contact pad 122 and the head contact pad 124 discussed later, the extending arm 130 may be contourable, pre-contoured, or modular such that different sizes and shapes may be selected by the surgeon to be attached directly or indirectly to the track 140. On the other end 132 of the extending arm 130 is a second contact pad 124 for the engagement of the soft tissue surrounding the metatarsal head proximate the pad 124. The contour of the head contact pad 124 may also be conformed during surgery to a shape that matches the soft tissue proximate the bone (e.g. concave) or pre-contoured. The head contact pad 124 may also be selectable by the surgeon from a plurality of different sizes and shapes, such that the jig 100 may have a set of interchangeable contact pads, or pads inserts that attach to the first end 132 of the arm 130. The arm 130 may include a longitudinal section 131, a lateral section 133 and a vertical section 135 to position the head contact pad 124. The longitudinal section 131 and the vertical section 135 may be adjustable by the surgeon to adjust the position of the head contact pad 124, or alternatively may be selectable from a plurality of sizes and shapes in the same manner discussed above.

Figure 7:
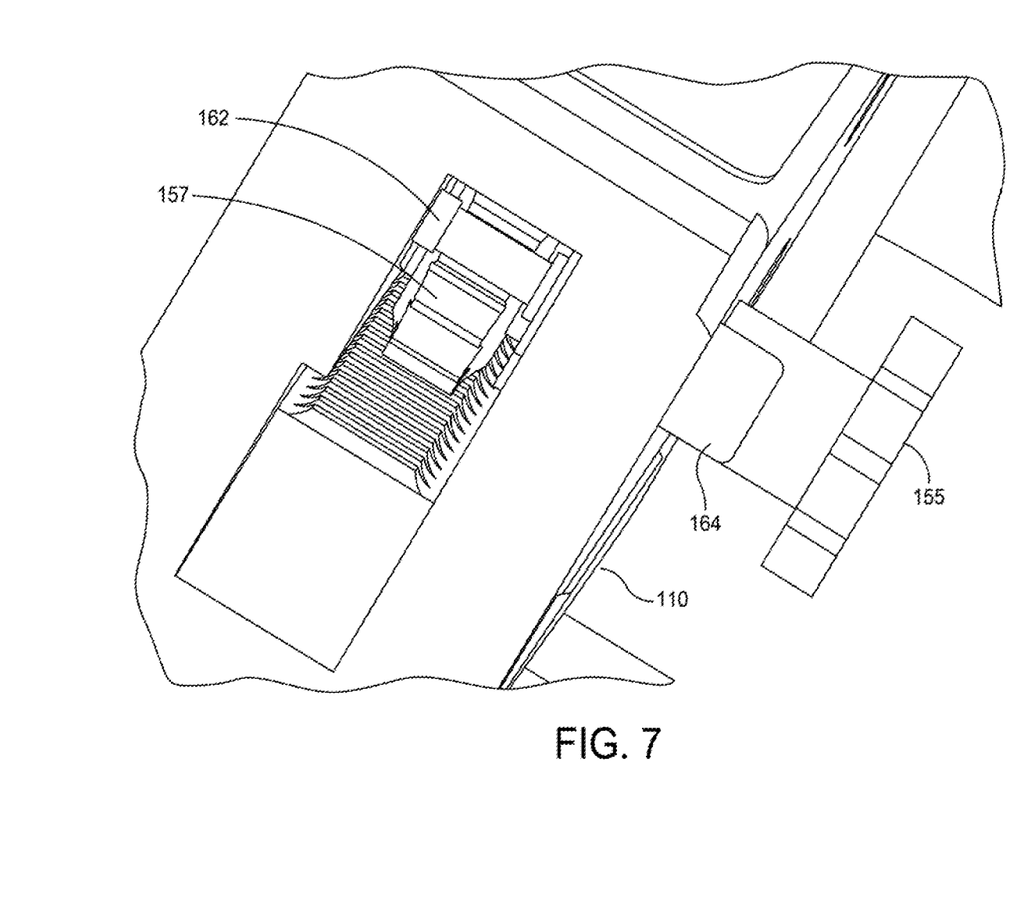
FIG. 7 illustrates the track drive and released lock in accordance with an embodiment of the disclosed subject matter.

A track drive 150 (see also, FIGS. 4, 7), including a manual knob 155, dial, or wheel is rotatably connected to the jig body 110, at least a portion of the knob or dial wheel extending outside the jig body 110 to be accessible for manual engagement. The track drive cooperating with the engagement mechanism of the track 140. As shown in FIGS. 1 and 7, the track drive 150 includes a circular gear with intermeshing teeth 157 that functions as a pinion in a rack and pinion mechanism, the rack and pinion may also engage frictionally with high friction surfaces on the pinion 150 and cooperating track 140. Alternatively, the track drive may be a worm drive, an internally threaded wheel of a lead screw mechanism, or a ball thread drive, each of which translates rotation of the knob, dial or wheel into linear lateral advancement of the track 140 (i.e., rotation of the track drive moves the track 140 and arm 130 laterally. Each increment of rotation of the circular drive (pinion) or length of track (rack) may be biased into position with known methods such as stop points achieved using teeth or ball plungers so that the track clicks into a plurality of positions laterally spaced from the jig body. Additionally, each increment may be of a predetermined measurement such as a mm or fraction thereof.

Figure 6A:
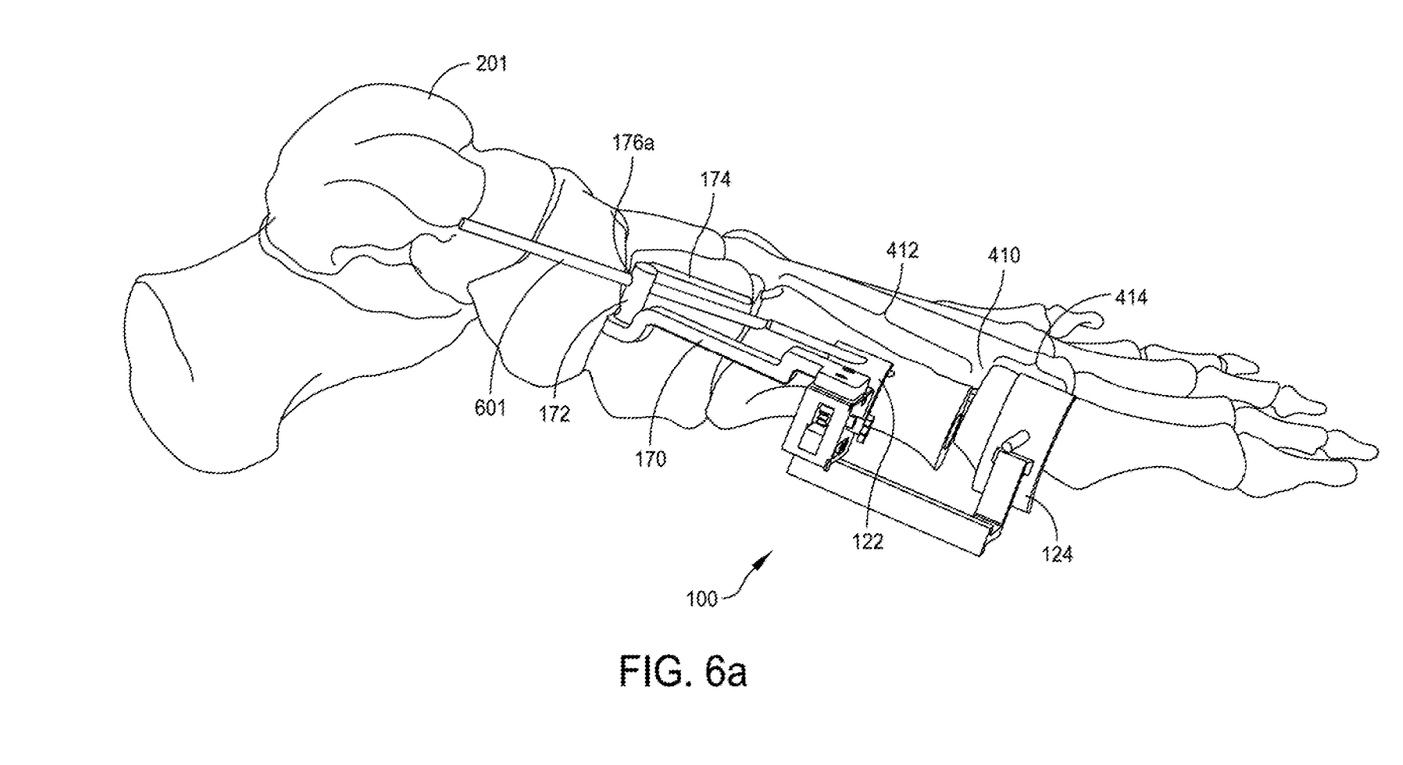
FIGS. 6A and 6B illustrate in a lateral and A-P view, respectively, the insertion of a guide wire into the metatarsal shaft and laterally displaced head via a visual guide on the translation and insertion jig in accordance with some embodiments of the disclosed subject matter.
Figure 6B:
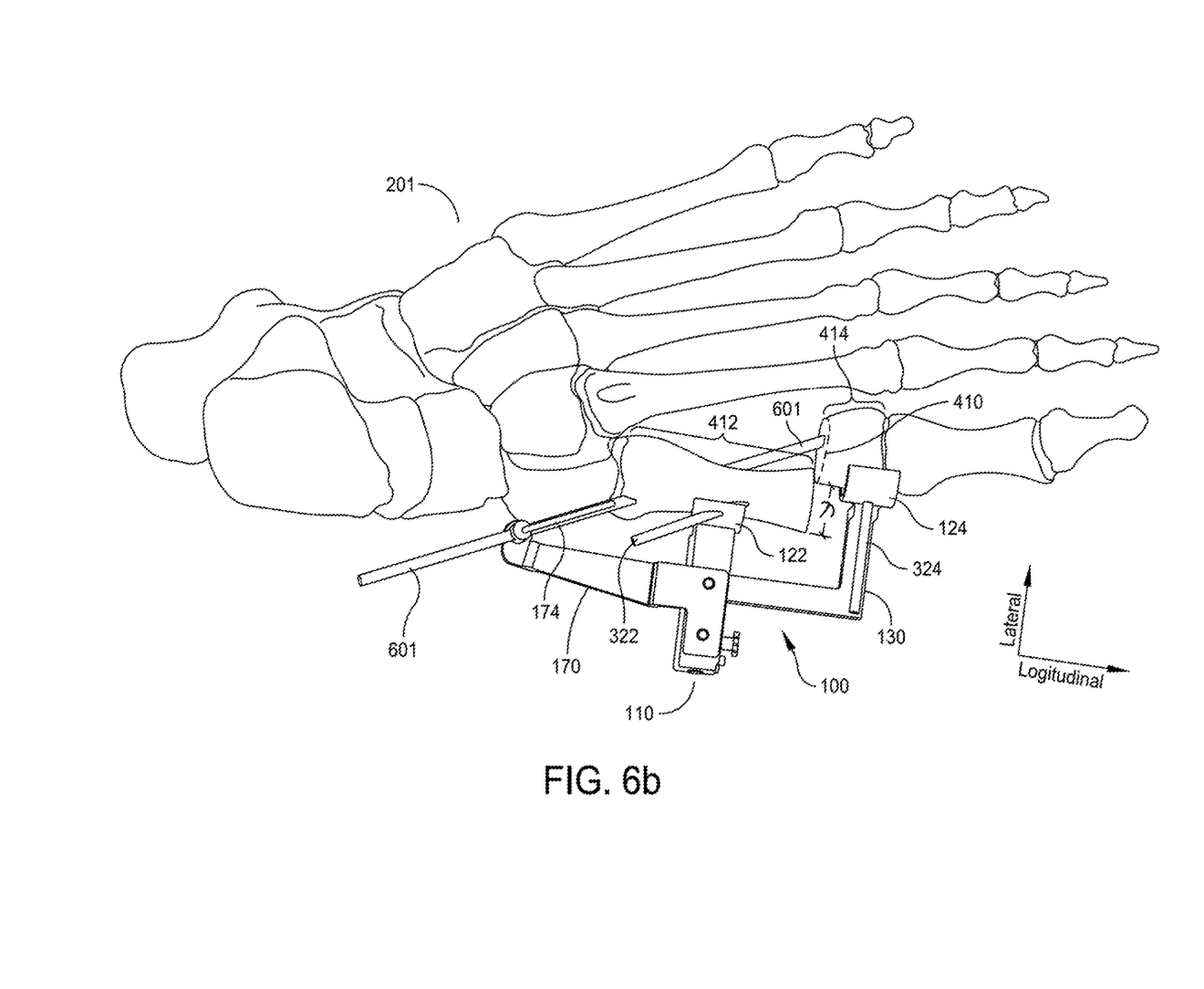

A track lock 160 is attached to the jig body 110 configured to selectively restrain the track from translation relative to the jig body 110. The track lock 160 when engaged prevents the track 140 from retracting laterally and in some embodiments prevents any lateral translation irrespective of direction. The track lock 160 may take the form of a ratchet, allowing the track to advance but not retract, an interlock 162 (as shown in FIG. 7) in which the lock 160 does not allow any translation. The track lock 160 is preferably biased in a locking position, freeing the surgeon from holding the jig to maintain the bone displacement. The track lock 160 may directly engage the track 140 to prevent its translation, or may engage the track drive 150 preventing it from rotating and thus restrict translating. The track lock 160 may alternatively be a threaded restraint screw (not shown) tightened to frictionally engage either the track 140 or drive 150, and loosened to release the same, or vice versa. The track lock 160, shown in FIGS. 3 and 6, is biased in the locked position by a spring 163 and released by pressing button 164 removing the interlock 162 from the pinion gears 157, as shown in FIG. 7. With respect to alternative embodiments in which the track drive 150 is a lead screw or worm drive, the mechanical configuration largely limits the need for a track lock 160 since the track 140 cannot drive the track drive 150, thus locking the track 140 in place.

An alignment/targeting guide arm 170 is removably attached to the jig body 110 and extends longitudinally from the jig body 110. A post 172 extends vertically from an end of the alignment guide arm, and visual alignment rod 174 is attached to the post which is selectively rotatable about a vertical axis with respect to the alignment guide arm 170 for establishing the desired trajectory in the A-P plane. Although not shown a second visual alignment rod which is selectively rotatable about a horizontal axis with respect to the alignment guide arm may also be beneficial in establishing the desired trajectory in the lateral plane. The post 172 may feature one or more holes 176a,b aligned with the alignment rod 174. These holes 176a,b may be beneficially sized to accept 3.0 mm and/or 4.0 mm MICA Screw k-wires, for insertion into the metatarsal portions using the jig 100. The visual alignment rod 174 may be created via hole in the vertical post 172 through which a k-wire is inserted to serve as the visual alignment rod 174 when fluoroscopy is used. The alignment guide 170 may also incorporate sleeves through which k-wires are inserted to ensure the wires enter the bone at the proper trajectory.

Figure 2:
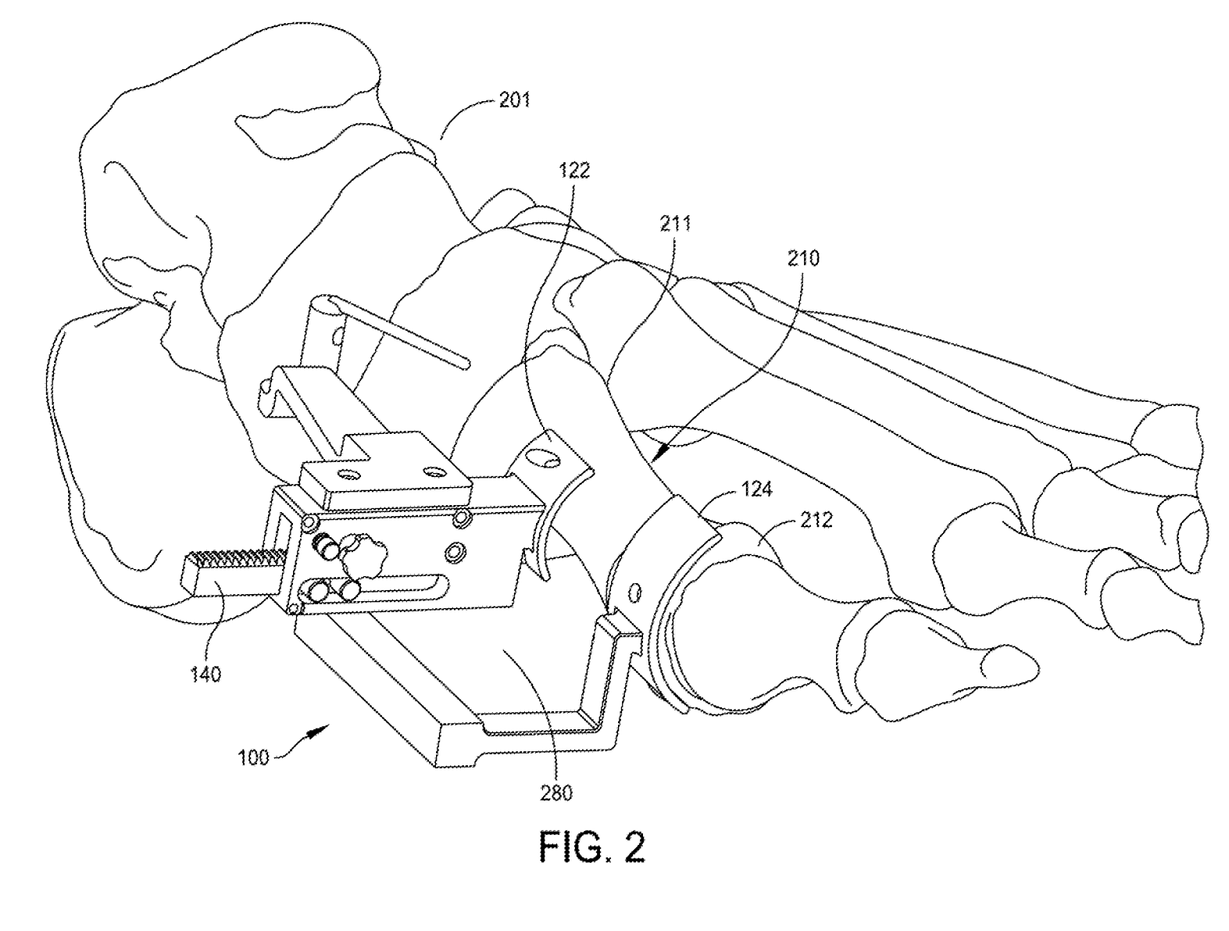
FIG. 2 illustrates the translation and insertion jig positioned on the soft tissue near the metatarsal bone of the foot in accordance with some embodiments of the disclosed subject matter.

FIG. 2 illustrates the jig 100 positioned on the soft tissue (not shown) proximate the metatarsal 210 of a foot 201. The shaft contact pad 122 is positioned upon the soft tissue covering the metatarsal shaft 211 and the head contact pad 124 is positioned upon the soft tissue covering the metatarsal head 212. As shown in FIG. 1, the track 140 and arm 130 are in the retracted or initial position. The extending arm 130 may be configured with respect to the anticipated incision location so as not to interfere with the osteotomy instruments access to the metatarsal bone 210 via the incision. As shown in FIG. 2, the shape of the extending arm 130 leaves an access area 280 to the metatarsal 210 between 270 and 360 degrees.

FIG. 3 illustrates the attachment of the jig 100 to the metatarsal bone 210 via k-wires 324 and 322. The respective k-wires 322 and 324 are inserted through holes 126 and 128 in contact pads 124 and 122 respectively through the soft tissue and into the shaft 211 and head 212 of the metatarsal 210. The holes 126 and 128 are preferably oriented to direct the k-wires into the bone to ensure multi-dimensional fixation of each of the contact pads 122 and 124 to the shaft 211 and head 212 of the metatarsal bone 210. The multi-dimensional fixation of each portion of the metatarsal bone 210 is desirable to ensure the jig 100 remains secured to the respective bone portions subsequent the osteotomy.

In FIG. 4, the jig 100 positioned on the metatarsal bone 210 is shown subsequent to the osteotomy 410. As a result of the osteotomy 410, the metatarsal 210 is divided into a shaft portion 412, including the shaft 211, being attached to the shaft contact pad 122 and a head portion 414 including the head 212 being attached to the head contact pad 124. The track 140 and extending arm 130 are shown in a retracted position or initial position prior to the translation of the head portion 414 with respect to the shaft portion 412 via the jig 100.

Figure 5:
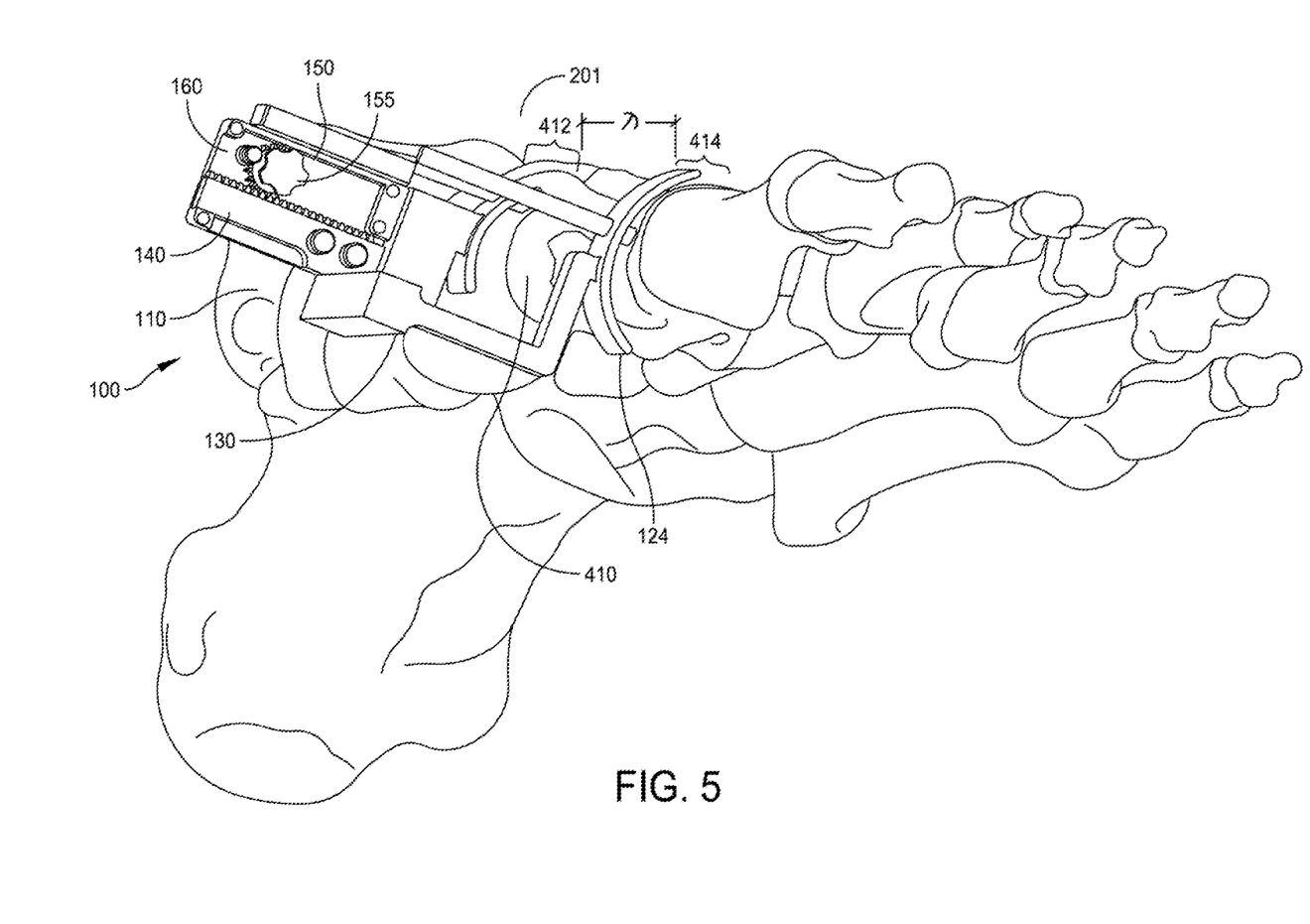
FIG. 5 illustrates the translation and insertion jig attached to the metatarsal bone subsequent to the lateral displacement of the metatarsal bone head via the jig in accordance with some embodiments of the disclosed subject matter.

FIG. 5 illustrates the jig 100 with the track 140, arm 130 and the head contact pad 124 extended to the desired location selected by the surgeon. As can be seen in FIG. 5, at the osteotomy 410, the head portion 414 has been translated laterally from the shaft portion 412 by λ. The track 140 is configured to laterally translate from a first position as shown in FIGS. 2, 3 and 4 to a fully translated position including any intermediate surgeon selectable position as shown in FIGS. 5 and 6B. The track 140 is restrained to a predetermined path, typically a straight line, however, it may be beneficial in some circumstances for the path to be curved or not linear.

Turning to FIGS. 6A and 6B, the insertion of the guide wire 601 through the shaft portion 412 and head portion 414 of the metatarsal 210 is shown. With the translation λ established and maintained via the jig 100, the k-wire 601 is placed through the k-wire hole (176a,b) in the post 172 and inserted into the metatarsal 210 following the trajectory established by visual guide rod 174. A screw may then be guided by the guide wire 601 into the shaft portion 412 and head portion 414 of the metatarsal to fix the translation λ throughout the healing period. Because of the lock 160 or the inherent nature of the track drive 150, the displacement λ is maintained by the jig 100 without the necessity of surgeon's attention or hands, which are freed for the insertion of the guide wire 601 and ultimately the fixation screw (not shown).

The visual guide 174 enables the surgeon to visualize the relative position of the surgical k-wire 601 within both portions of the bone 210. FIG. 6B illustrates an anterior posterior (A-P) view, i.e. looking down upon the foot 201. The visual guide rod 174 is coincident with the surgical k-wire 601 when the k-wire 601 is following the prescribed trajectory in the A-P view as shown in FIG. 6B. If a second visual guide is provided, it would be coincident with the surgical k-wire 601 when the k-wire 601 is following the prescribed trajectory in the lateral view, generally shown in FIG. 6A. Thus the location and movement of the inserted k-wire 601 in the A-P view may be represented by the visual guide rod 174, additionally, the visual guide rod 174 may also be rotatable with respect to the horizon and thus act as an insertion guide in the lateral plane (i.e. the plane normal to the lateral direction), though it requires the surgeon to account for the vertical offset in the lateral view. Likewise, in FIG. 6A, the second guide rod (not shown) may govern movement of the inserted k-wire 601 in the lateral plane. Thus between the top and side views of FIGS. 6A and 6B respectively, the location and trajectory of the inserted k-wire 601 may be represented in three dimensions and thus monitored and controlled using one or two visual guide rods.

Figure 8:
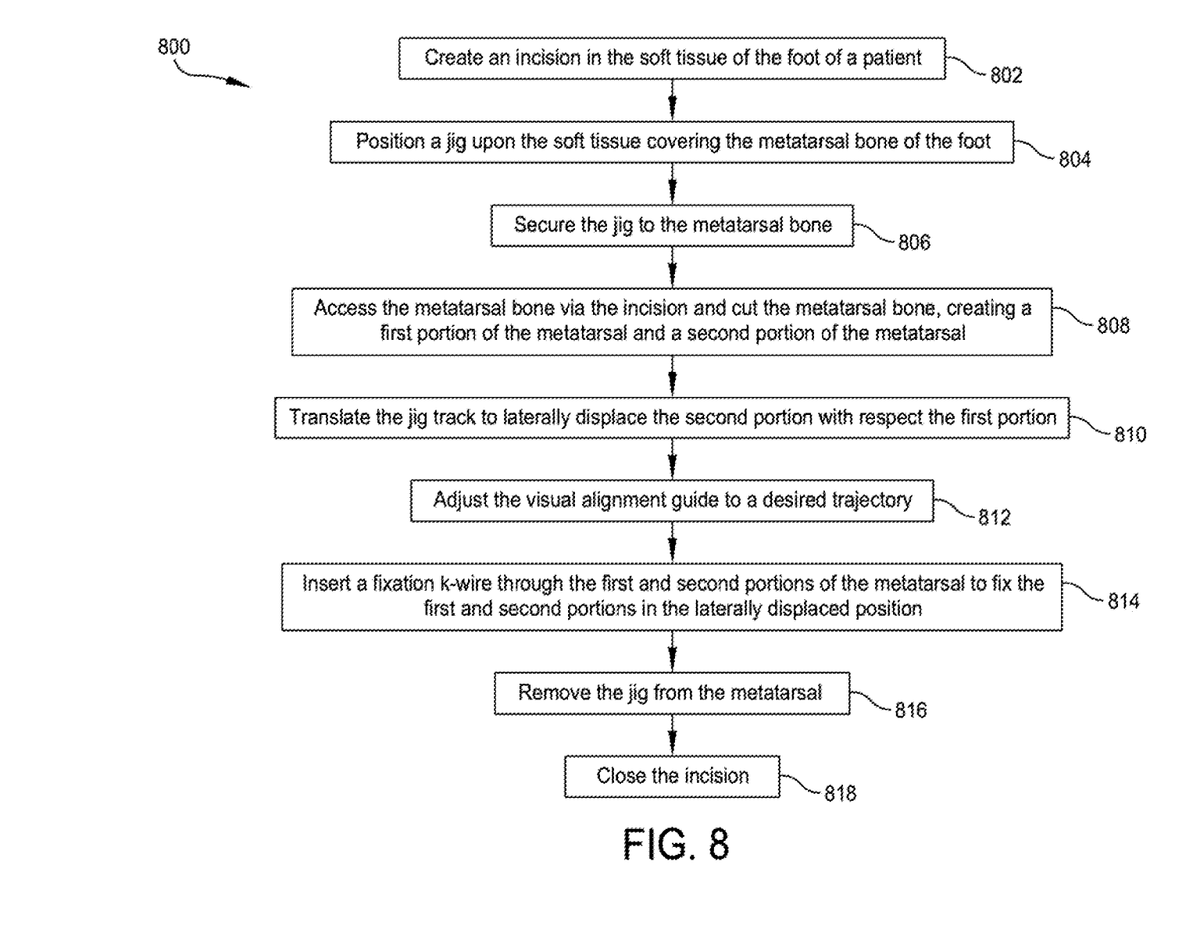
FIG. 8 is a flow chart of a method of performing MIS bunion surgery with the translation and insertion jig in accordance with embodiments of the disclosed subject matter.

FIG. 8 illustrates a method 800 for performing a percutaneous bunionectomy using the jig 100. First, as is common in a conventional percutaneous bunionectomy, an incision in the soft tissue of the foot 201 of a patient is created by the surgeon as shown in Block 802. The jig 100 is positioned upon the soft tissue (not shown) proximate the metatarsal bone 210 of the foot 201 as shown in Block 804 (see also FIG. 2 which illustrates the jig 100 on the soft tissue proximate the metatarsal 210). As properly positioned, the shaft contact pad 122 and a head contact pad 124 of the jig 100 are proximate the shaft 211 and head 212 respectively of the metatarsal bone 210.

In Block 806, the jig 100 is secured to the metatarsal bone 210 as illustrated in FIG. 3. In FIG. 3, the jig 100 is secured to the bone via k-wires 322 and 324 inserted through the contact pads, soft tissue and into the bone, however it is envisioned other fastening devices (i.e. screws, pins, clamps etc.) may also have beneficial applications.

In Block 808, the metatarsal bone is accessed through the incision and is cut creating first and second portions 412 and 414 of the metatarsal 210, the result of the osteotomy 410 is illustrated in FIG. 4. The jig track 140 is then translated by manually rotating knob 155 of the track drive 150 such that the desired displacement λ is achieved between the two portions as shown in Block 810. FIG. 5 illustrate the track 140, arm 130, head contact pad 124 and head portion 414 of the metatarsal with the desired displacement λ. As noted above, the locking mechanism 160 or the mechanical configuration of the track drive 150 prevents the track 140 from retracting, thus in some embodiments, the locking mechanism must be activated subsequent translation, or in the case where the locking mechanism 160 is biased in a locking position, the locking mechanism would be released to allow the translation of the track 140.

As shown in Block 812, the visual guide rod 174 of the alignment guide 170 is adjusted to the desired trajectory. FIG. 6B illustrates the visual guide rod 174 aligned along the surgeon selected trajectory. In Block 814, a guide wire is inserted through the first and second portions 412 and 414 of the metatarsal 210 to fix the first and second portions in the laterally displaced position. FIG. 6A illustrates the k-wire 601 inserted through the shaft portion 412 and the head portion 414 when they are displaced by λ. The surgical k-wire 601 is positioned through one of the guide holes 176a, 176b and into the soft tissue of the foot 201. The k-wire 601 is advanced while aligning it with the visual guide rod 174 in the A-P plane, and if a second guide rod is provided, then aligning the k-wire 601 with the other guide rod in the lateral plane. The surgeon may check the position in both A-P and lateral planes to determine trajectory of surgical k-wire and adjust as needed. These latter steps typically require use of fluoroscopy to confirm intended trajectory has been achieved. The surgical k-wire 601 is advanced into the bone while maintaining the desired trajectory in the lateral and A-P planes with reference to the respective visual guides. The surgical k-wire may be advanced incrementally and its position and orientation again verified via the visual guide as it is advanced. As noted, a fluoroscope is preferably used to visualize the bone and the surgical k-wire with reference to the visual guide. Thus, it is preferable that the visual guide rod 174 is not X-ray permeable, so it will appear on the fluoroscope. As shown in Block 816, the jig 100 is removed from the metatarsal 210. Subsequent removal of the jig 100, the surgeon may use a depth gage placed over the guide k-wire 601 to measure screw length. The surgeon then places a drill over the k-wire 601 with a cannulated drill, then inserts a fixation screw over the k-wire to properly fixate the osteotomy. The guide wire 601 is then removed. A second screw may also be placed lateral to this screw depending on patient anatomy and needs. The incision is closed in Block 818.

The visual guide 170, as discussed above, may have one or more guide rods that extend parallel to the surgical k-wire and serve as representations of the surgical k-wire within the respective planes, to assist in its proper insertion.

Another aspect of the disclosed subject matter is that the visual guides may be any narrow elongated straight rod, strip or bar that achieve the desired goal of visually referencing the position of the surgical k-wire being inserted. Examples may be rods formed from plastic, ceramic, metal or organic material, or composites thereof. For materials that are x-ray permeable, non-permeable material may be added to enable the guide to be visible under a fluoroscope.

While the jig 100 shown in FIGS. 1-7, is configured for the left foot, it is equally envisioned that the jig could be likewise configured for the right foot, or even configured for universal use on both the left and right feet with minor adjustments as understood by one skilled in the art. Additionally, although the disclosed subject matter is described with respect to a rack and pinion system (i.e. the track is the rack and the drive is the pinion) other configurations are also envisioned, such as a worm drive for translating the track, ball-screw drive system, or a lead screw system. Additionally, while the lock is described with respect an interlock key, other configurations, such as a frictional lock or ratcheting lock are also envisioned.

The method shown in FIG. 8, describes the positioning and securing of the jig 100 prior to the creation of the incision, and/or the osteotomy. However, one or both of the incision and the osteotomy may be performed prior to the positioning and/or securing of the jig 100. In the case where the osteotomy is preformed prior to the securing of the jig 100, the jig 100 need not account for access 280 to the bone 210, other than for the guide wire 601 and subsequent fixation screw.

Another aspect of the disclosed subject matter is that although the jig 100 is described in view of minimally invasive bunion surgery, it may also be useful in other osteotomies in which portions of a bisected bone are displaced relative to one another, as may be appreciated by those skilled in the art.

Although the methods described above are with reference to the illustrated flowchart, it will be appreciated that many other ways of performing the acts associated with the methods can be used. For example, the order of some operations may be changed, and some of the operations described may be optional.

The foregoing is provided for purposes of illustrating, explaining, and describing embodiments of these disclosures. Modifications and adaptations to these embodiments will be apparent to those skilled in the art and may be made without departing from the scope or spirit of these disclosures.

What is claimed is:

1. A system for performing a percutaneous bunionectomy in a metatarsal including a metatarsal shaft and a metatarsal head, comprising:
   a jig comprising:
      a jig body extending in a lateral direction between a first body end and an oppositely disposed second body end;
      a metatarsal shaft contact pad connected to the first body end, and configured to conform to a portion of soft tissue proximate to the metatarsal shaft;
      an arm extending in a longitudinal direction from the jig body, the arm having a first arm end and a second arm end;
      a metatarsal head contact pad connected to the first arm end, and configured to conform to a portion of the soft tissue proximate to the metatarsal head;
      a linear track extending in the lateral direction, the track rigidly connected to the second arm end and movably connected to the jig body, the track including an engagement mechanism;
      a circular drive rotatably connected to the jig body, the circular drive cooperating with the engagement mechanism of the track, such that a rotation of the circular drive results in a lateral movement of the track;
      a lock connected to the jig body and configured to restrain the track from translation relative to the jig body by selectively engaging the engagement mechanism of the track or the circular drive; and
      an alignment guide arm, the alignment guide arm connected to and extending longitudinally from the jig body;
   a plurality of positioning k-wires, wherein each of the metatarsal head contact pad and the metatarsal shaft contact pad, comprise a multi-dimensional fixation hole configured to receive one of the plurality of positioning k-wires; and
   at least one fixation guide k-wire.

2. The system of claim 1, further comprising a lock connected to the jig body and configured to selectively restrain the track from lateral translation relative to the jig body.

3. A method for performing a percutaneous bunionectomy, comprising:
   providing the system of claim 1;
   creating an incision in the soft tissue enveloping the foot of a patient;
   positioning the jig upon the soft tissue proximate a metatarsal bone of the foot;
   securing the jig to the metatarsal bone;
   translating the jig track to laterally displace a second portion of the metatarsal bone with respect a first portion of the metatarsal bone;
   locking the jig so as to restrain translation by selective engagement with the jig track;
   adjusting a visual alignment guide to a desired trajectory;
   inserting the at least one fixation k-wire through the first and second portions of the metatarsal to fix the first and second portions in the laterally displaced position;
   removing the jig from the metatarsal; and
   closing the incision.

4. The method of claim 3, further comprising accessing the metatarsal bone via the incision and cutting the metatarsal bone, creating the first portion of the metatarsal and the second portion of the metatarsal.

5. The method of claim 3, further comprising the steps of installing internal fixation hardware using the at least one fixation k-wire and removing the at least one fixation k-wire prior to closing the incision.

6. The method of claim 3, wherein the step of positioning the jig upon the soft tissue proximate the metatarsal bone of the foot comprises positioning the shaft contact pad and the head contact pad of the jig on the soft tissue of the foot proximate the shaft and head, respectively, of the metatarsal bone.

7. The method of claim 3, wherein the step of securing the jig to the metatarsal bone comprises inserting the positioning k-wire through the multi-dimensional fixation holes in each of the shaft contact pad and head contact pad, through the soft tissue and into the shaft and head, respectively, of the metatarsal.

8. The method of claim 3, wherein the step of translating the jig track comprises rotating a drive knob and locking the track into position.

9. The method of claim 3, wherein the step of inserting the at least one fixation k-wire through the first second portions of the metatarsal comprises aligning the at least one fixation k-wire with the visual alignment guide.

10. The method of claim 9, wherein the step of inserting the at least one fixation k-wire through the first and second portions of the metatarsal further comprises checking the alignment under a fluoroscope.

11. An adjustable jig for minimally invasive bunion surgery, comprising:
   a jig body extending in a lateral direction between a first body end and an oppositely disposed second body end;
   a metatarsal shaft contact pad connected to the first body end, and configured to conform to a portion of soft tissue proximate the metatarsal shaft;
   an arm extending in a longitudinal direction from the jig body, the arm having a first arm end and a second arm end;
   a metatarsal head contact pad connected to the first arm end, and configured to conform to a portion of soft tissue proximate the metatarsal head;
   a linear track extending in the lateral direction, the track rigidly connected to the second arm end and movably connected to the jig body, the track including an engagement mechanism;
   a circular drive rotatably connected to the jig body, the circular drive cooperating with the engagement mechanism of the track, such that a rotation of the circular drive results in a lateral movement of the track; and,
   a lock connected to the jig body and configured to selectively restrain the track from translation relative to the jig body wherein the lock is configured to selectively engage the engagement mechanism of the circular drive to restrain the track.

12. The adjustable jig of claim 11, further comprising an alignment guide arm, the alignment guide arm connected to and extending longitudinally from the jig body.

13. The adjustable jig of claim 11, wherein the engagement mechanism comprises a plurality of teeth and circular drive comprises a plurality of intermeshing teeth.

14. The adjustable jig of claim 11, wherein the engagement mechanism comprises a high friction surface.

15. The adjustable jig of claim 12, wherein the lock is biased to restrain the track.

16. The adjustable jig of claim 11, wherein the metatarsal head contact pad and the metatarsal shaft contact pad are concave.

17. The adjustable jig of claim 11, wherein each of the metatarsal head contact pad and the metatarsal shaft contact pad, comprise a k-wire multi-dimensional fixation hole.

18. The adjustable jig of claim 12, further comprising a post extending vertically from an end of the alignment guide arm, and a visual alignment rod attached to the post and selectively rotatable about a vertical axis with respect to the alignment guide arm.

19. The adjustable jig of claim 13, further comprising a second visual alignment rod selectively rotatable about a horizontal axis with respect to the alignment guide arm.

20. The adjustable jig of claim 11, wherein the circular drive engages with the engagement mechanism within the jig body, the circular drive further comprising a drive knob, a portion of the knob external to the jig body.

21. The adjustable jig of claim 11, wherein the linear track is a rack and the circular drive is a pinion.

22. The adjustable jig of claim 11, wherein the jig body further restraining the linear track longitudinally to a pre-determined path.

23. The adjustable jig of claim 18, wherein the post defines a hole for receiving a guide wire.

\* \* \* \* \*